United States Patent [19]

Sahatjian et al.

[11] Patent Number: 5,306,246
[45] Date of Patent: Apr. 26, 1994

[54] BALLOON FOR MEDICAL CATHETER

[75] Inventors: Ronald Sahatjian, Lexington; Arthur R. Madenjian, Winchester, both of Mass.

[73] Assignee: Boston Scientific Corporation, Watertown, Mass.

[21] Appl. No.: 943,977

[22] Filed: Sep. 11, 1992

Related U.S. Application Data

[63] Continuation of Ser. No. 612,073, Nov. 9, 1990, abandoned.

[51] Int. Cl.$^5$ ............................................. A61M 29/00
[52] U.S. Cl. ...................................... 604/96; 264/515; 428/36.9
[58] Field of Search ........................ 604/96; 264/515; 428/36

[56] References Cited

U.S. PATENT DOCUMENTS

| | | | |
|---|---|---|---|
| 3,141,912 | 7/1964 | Goldman et al. | 264/95 |
| 3,162,190 | 12/1964 | Del Gizzo | 128/6 |
| 3,448,739 | 8/1969 | Stark et al. | 128/2.05 |
| 3,533,265 | 10/1970 | Valks | 72/270 |
| 3,865,666 | 2/1975 | Shoney | 156/245 |
| 4,072,147 | 2/1978 | Hett | 128/6 |
| 4,093,484 | 6/1978 | Harrison et al. | 156/244.13 |
| 4,130,617 | 12/1978 | Wallace . | |
| 4,146,019 | 3/1979 | Bass et al. | 128/6 |
| 4,154,244 | 5/1979 | Becker et al. | 128/349 |
| 4,195,637 | 4/1980 | Grüntzig et al. . | |
| 4,224,929 | 9/1980 | Furihata | 128/5 |
| 4,254,774 | 3/1981 | Boretos | 128/348 |
| 4,256,789 | 3/1981 | Suzuki et al. | 428/35 |
| 4,313,431 | 2/1982 | Frank | 128/7 |
| 4,367,747 | 1/1983 | Witzel | 128/344 |
| 4,410,482 | 10/1983 | Subramanian | 264/515 |
| 4,411,055 | 10/1983 | Simpson et al. | 29/447 |
| 4,416,942 | 11/1983 | Di Luccio | 428/332 |
| 4,444,817 | 4/1984 | Subramanian | 428/36 |
| 4,470,407 | 9/1984 | Hussein | 128/6 |
| 4,490,421 | 12/1984 | Levy | 428/35 |
| 4,943,460 | 7/1990 | Markle et al. | 428/36.9 |
| 4,946,743 | 8/1990 | Winter | 428/249 |
| 4,952,628 | 8/1990 | Blatz | 525/58 |
| 4,963,313 | 10/1990 | Noddin et al. | 264/573 |
| 4,964,409 | 10/1990 | Tremulis | 128/673 |
| 5,017,325 | 5/1991 | Jackowski et al. | 264/521 |

FOREIGN PATENT DOCUMENTS

| | | |
|---|---|---|
| 0341587 | of 0000 | European Pat. Off. . |
| 0274411 | 7/1988 | European Pat. Off. . |
| 0318919A2 | 6/1989 | European Pat. Off. . |
| 0420488 | 4/1991 | European Pat. Off. . |
| 61009433 | of 0000 | Japan . |
| 57-48377 | 10/1982 | Japan . |

OTHER PUBLICATIONS

Selar PT Barrier Resin Product Literature.
Fetell In "Barrier Breakthrough-Selar Barrier Resin", *High Performance Container Technology:* Second Low Molding Technical Conference, Itaca, Ill., Nov., 1985.
"New Ideas in Blow Molding: Laminar Barrier Containers", *Modern Plastics*, p. 94 (May, 1985) Abstract.
Levy, "Improved Dilatation Catheter Balloons", *J. of Clin. Eng.* XI:4 (Jul./Aug. 1986).
Microvasive Product Literature.
Product Literature Selar PT 4368/Barrier Resin.

*Primary Examiner*—John D. Yasko
*Assistant Examiner*—Ronald Stright, Jr.
*Attorney, Agent, or Firm*—Fish & Richardson

[57] ABSTRACT

An inflatable medical dilation balloon and methods for forming the same wherein the balloon member is comprised of a polymer bled including a predominant amount of a crystalline polymer, e.g. a polyester, and a compliance enhancing additive polymer, e.g. a polyolefin, in amount sufficient to interrupt the crystalline structure of the crystalline polymer. The amount is about 20% or less of the polymer blend. The balloon member formed of the polymer blend is inflatable for medical dilation, e.g. of the prostrate.

30 Claims, 2 Drawing Sheets

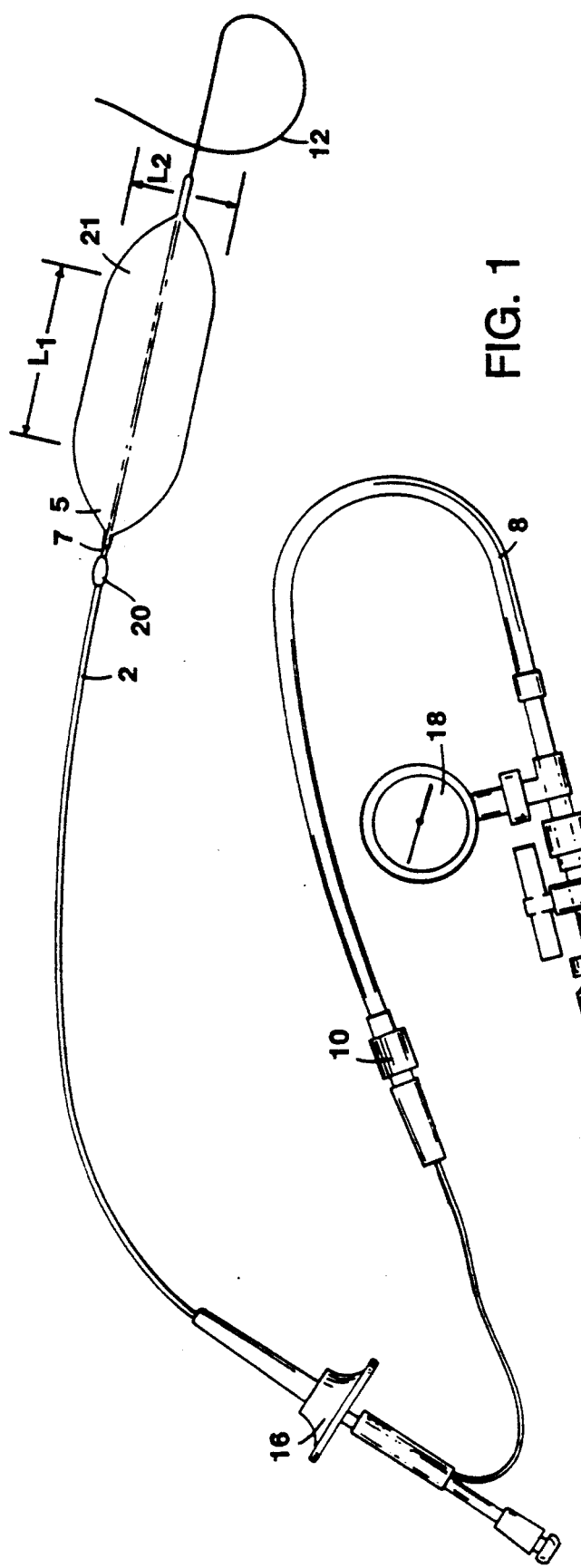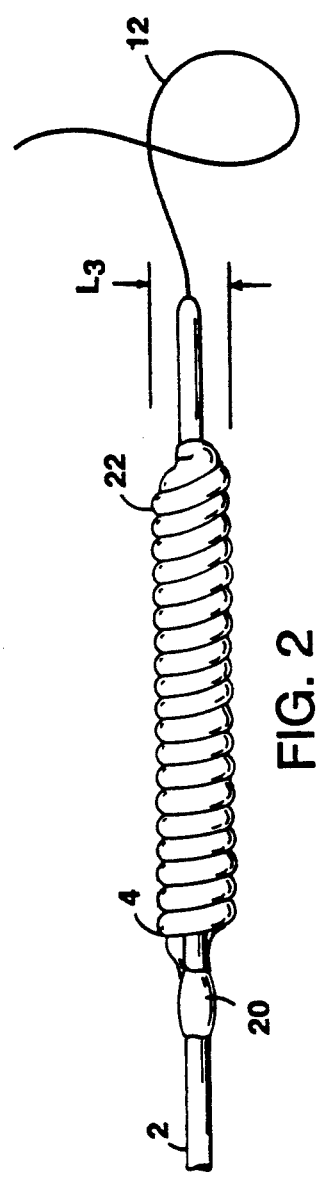
FIG. 1
FIG. 2

BALLOON FOR MEDICAL CATHETER

This is a continuation of application Ser. No. 07/612,073, filed Nov. 9, 1990, now abandoned.

FIELD OF THE INVENTION

This invention relates to balloons for medical catheters.

BACKGROUND OF THE INVENTION

Medical Balloons are intended to be collapsed about their long supporting devices. In the case of balloon catheters for, for example, prostate dilatation, a small size catheter is necessary to enable advancement of the catheter through the urethra and into the prostate where the balloon is to be inflated to sufficient pressure and without bursting so that the dilatation procedure may be accomplished. After use, the balloon must be deflated and withdrawn.

SUMMARY OF THE INVENTION

In a first aspect, the invention features an inflatable dilation balloon for medical use. The balloon is composed of a polymer blend including a major amount of a crystalline polymer and a relatively minor amount of an additive polymer that interrupts the crystalline structure of the crystalline polymer, resulting in enhanced compliance.

Particular embodiments may include one or more of the following features. The additive is incompatible with the crystalline polymer. The additive forms domains within the blend. The additive is compatible with the crystalline polymer. The additive is an amorphous polymer. The additive is a polyolefin. The additive is polyethylene. The additive is a crystalline polymer. The additive is a liquid-crystal polyester material. The additive is a preblend. The additive is a preblend of PET and polyethylene. The preblend is Selar PT ®. The additive is about 20% or less of the polymer blend. The additive is between about 5 to 10% of the polymer blend.

Particular embodiments may also include one or more of the following. The crystalline polymer is high molecular weight PET. The PET has an intrinsic viscosity of about 0.7 or greater. The balloon is adapted for dilatation of the prostate. The balloon wall has a thickness of about 0.0015 inch or less. The balloon has a burst pressure of more than 6 atmosphere. The balloon has a burst pressure of 4 to 8 atmosphere. The balloon has a hoop stress at failure of greater than about 36,000 psi. The balloon exhibits enhanced compliance over PET of about 25% or more with decreased hoop stress of about 10% or less. The polymer blend is free inflated to form the balloon.

In another aspect, the invention features a catheter for dilatation. The catheter includes a catheter shaft carrying for inflation at its distal end, a dilation balloon. The balloon is composed of a polymer blend including a major amount of a relatively noncompliant polymer and a minor amount of a relatively compliant additive polymer, the blend resulting in a balloon of enhanced compliance.

In another aspect the invention features a method for forming a medical balloon. The method includes preparing a polymer blend of a major amount of a crystalline polymer with a relatively minor amount of an additive polymer that interrupts the crystalline structure of the crystalline polymer and forming the blend into a balloon resulting in enhanced compliance.

Particular embodiments may include one or more of the following. The preparing includes blending a crystallizable polymer with the additive, and crystallizing the polymer. The forming includes free inflation of the polymer blend. The crystalline polymer is blended with an additive in the form of a preblend. The preblend is Selar PT.

Other aspects and embodiments follow.

DESCRIPTION OF THE PREFERRED EMBODIMENT

We first briefly describe the drawings.

DRAWINGS

FIG. 1 is a schematic of a balloon catheter for prostate dilation, employing a balloon according to the invention.

FIG. 2 is an enlarged schematic of the balloon in FIG. 1, in the deflated state, prior to entry into a vessel.

STRUCTURE

Figure 3:
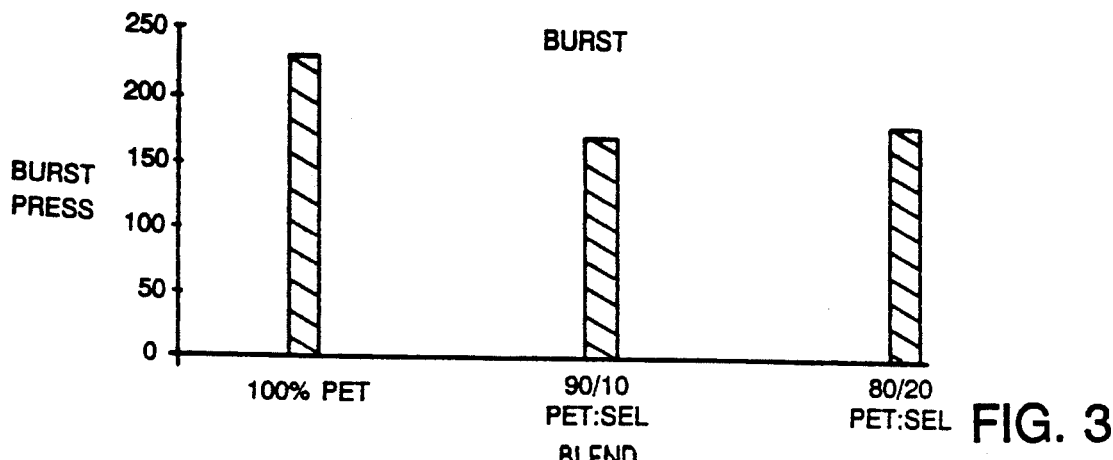
FIG. 3 is a bar graph comparing the burst pressure of a balloon formed of 100% PET and two balloons formed according to the invention.

Referring to FIG. 1, a balloon catheter for dilation of the prostate is shown to include a polyethylene catheter shaft 2 (12french) carrying at its distal end a dilation balloon 4 having a maximum inflated diameter $L_2$, about 30 mm and a length along the maximum inflated diameter of $L_1$, about 5 cm. The balloon includes taper regions 5 and regions 7 where the balloon is attached to the catheter. The balloon is a 90 french balloon, formed out of a polymer blend according to the invention as will be further discussed below. The balloon may be inflated and pressurized (e.g., from 4 to 8 atmospheres) with a LeVeen inflator 6 which passes inflation fluid through a tubing 8 that mates through a connector 10 to a balloon lumen 2 terminating in an inflation port (not shown) within the balloon 4. The catheter shaft 2 carrying the balloon 4 may be tracked over a guidewire 12 which passes through an additional lumen (not shown) within the shaft 2 and is introduced through a collar 16. The apparatus further includes a pressure gauge 18 for monitoring the inflation pressure and a positioning nodule 20 which permits precise placement with transrectal digital control so that dilation is not extended through the external sphincter and eliminates the need for cystoscopy or fluoroscopy. Retraction collar 16 permits hand traction for maintaining precise positioning during dilation.

Referring now to FIG. 2, the balloon is shown in the deflated position, prior to introduction into the body lumen. As illustrated, the balloon 4 is wrapped by wing-folding about the catheter shaft 2 and has a profile of $L_3$, about 0.182–0.195 inch. The purpose of the wrapping and folding of the balloon is to minimize the deflated profile so that the catheter may be passed through the body lumen to the desired point of treatment. As shown, in the deflated condition, the balloon includes a series of folds 22 that extend to radial diameters ($L_3$), greater than the outer diameter of the catheter body.

These folds 22 will typically engage the inner walls of the body lumen as the catheter is torqued to the position of treatment.

The balloon is composed predominantly of a blend of crystallizeable resin and an additive that interrupts the crystalline network of the crystalline resin in the final product. When the blend is formed into a balloon, the balloon exhibits advantageous properties of softness, i.e., compliance and a low folded profile, yet achieves high hoop stress and consequently high burst pressures. The balloon in the deflated state will thus yield when challenged by the wall of the lumen, yet can be inflated to high pressure for performing the dilatation procedure with reduced risk of burst. The crystallizeable resin is preferably a polyester, such as PET. The additive is generally 20% or less by weight of the blend, preferably in the range of about 5 to 10%. The additive may be compatible, i.e., miscible (there is a statistical distribution of the blend components and the thermodynamic properties of the additive are not separable from the properties of the blend), or incompatible. The additive forms domains within the crystalline polymer that interrupts the crystalline structure and thus modifies the properties of the crystalline polymer. The domains themselves may be single molecules of the additives which may occur with additives compatible with the crystallizeable polymer or an aggregate of additive molecules, typical of additives incompatible with the crystallizeable polymer (however with sufficient mechanical mixing, small, molecular domains may be achievable with incompatible additives.) Mixing of the polymer blend may be achieved by high shear methods such as micronized dispersion, as employed by manufacturers of polymer blends such as E. I. Dupont. The additive may be crystalline or amorphous. Crystalline additives include, liquid crystalline polymers (ordered fluids that demonstrate crystalline behavior). Examples of compatible liquid crystal polymeric polyester additives include Vectra ® (available from Hoeschst Corp.), Xydor ® (available from Amoco Corp.), and Rod Run ® (available from Eastman Kodak). Examples of non-crystalline additives include polyolefins such as polyethylene. Non-compatible additives of non-crystalline nature are preferred since the domains of non-crystalline material generally cannot complement or reinforce the crystalline structure of the crystalline polymer.

In particular embodiments, the balloon is composed of a minor amount of heterogeneous, preblended, polyolefin (e.g. polyethylene) and a polyester (e.g. PET); the preblend is then blended with a relatively high molecular weight PET. Suitable polyolefins and polyesters for forming the preblend and methods for blending incompatible polymers are known and are discussed in U.S. Pat. No. 4,444,817 entitled "Process for Making Laminar Articles of Polyolefins and Condensation Polymer", by Subramanian, the entire contents of which are hereby incorporated by reference. The polyolefin is, for example, polyethylene, polypropylene, polybutylene or copolymers of these materials and may be of high, medium or low density. The condensation polymers may be a polyamide, or polyester such as PET or polycarbonates. Typically, a compatiblizer is used. Suitable compatiblizers include alkylcarboxyl-substituted polyolefins, e.g., the polymerization product of an α-olefin with an olefinic monomer having acid groups or a polyethylene and copolymer of ethylene and at least one α-olefin of 3-8 carbon atoms such as polypropylene, which might be formed by grafting. Compatibilizers are further discussed in U.S. Pat. No. 4,444,817, supra. To form the preblend, the polymer particles may be mixed by high shear techniques such as micronized dispersion and by other techniques discussed in U.S. Pat. No. 4,444,817.

The balloon may be formed by free inflation of the polymer blend to crystallize the crystallizeable polymer and form a biaxially oriented polymer, as discussed in U.S. Pat. No. 4,963,313 entitled, "Balloon Catheter" by Noddin et al., the entire contents of which are hereby incorporated by reference. Alternatively, the blend could be blow molded.

In particular embodiments, the balloon may be formed using a commercially available preblend polymer resin of the type used in barrier films in the packaging industry, such as the toughened PET, Selar PT resin (preferred available as Selar PT 4368 from E. I. DuPont de Nemours and Company, Wilmington, Del.), which is a preblend of polyolefin and PET. In general, a minor amount of about 5 to 10%, generally not exceeding 20% of Selar PT resin is blended with high molecular weight PET (about 0.7 or greater intrinsic viscosity, weight average molecular weight about 46,800, e.g., 0.8 internal viscosity of 0.8, with weight average molecular weight of 56,450) and the polymer blend free inflated to form the balloon.

Balloons having dimensions, as described with respect to FIG. 1, and having a wall thickness of about 0.0006 inch may be formed by free inflation that exhibit burst pressures of 4 to 8 atmospheres, yet the material is relatively soft and compliant compared to balloons formed from PET. Typically, the balloons are at least about 25% more compliant (as indirectly measured by the percentage change in percentage increase in inflated length or diameter) than PET balloons of similar construction, yet the hoop stress at failure and burst pressure are not significantly reduced, e.g., hoop stress at failure is reduced typically less than about 10%.

The balloons of the invention may be formed by employing a blend of major amount of low compliance, relatively stiff polymer material, e.g., PET and a minor amount of a high compliance, softer polymer. While not wishing to be limited to any one theory, the properties of the balloons according to the invention are believed to be due to the interruption of the crystallizeable polymer. For example, in a particular embodiment employing PET and polyethylene, the PET, because it is crystalline, contributes the strength and high burst properties but is, itself, a relatively stiff, non-compliant material that upon deflation exhibits a relatively traumatic profile to the lining of the body lumen under treatment. Polyolefin contributes properties of improved softness or compliance such that the balloon may yield (e.g., deflect or compress) when challenged by the wall of a body lumen by interrupting the crystalline structure of the PET. The blend of these components does not, however, greatly reduce the strength of the balloon.

EXAMPLES

EXAMPLE I

In formulating the polymer blend less than about 20% by weight of Selar PT resin is mixed with bottle grade PET (Clear Tuf ® 8006, available from Good-Year). The components are mixed mechanically by conventional methods such as with an extruder. Balloons may be formed by free inflation as discussed in U.S. Pat. No. 4,963,313, incorporated supra. A tube of the polymer blend of which the balloon is to be composed is provided. A portion of the tube is crystallized to render it dimensionally stable under heated conditions. The tube is immersed in a heated bath of glycerin at a drawing temperature (e.g., 120° C.). Both the crystallized region and a short portion of the amorphous region of the tube are fully immersed in the tube. The portion of the tube out of the bath is gripped by a clamp and the crystallized portion of the tube submerged in the bath is gripped by an additional, movable clamp. After a suitable duration of immersion to insure that the resin reaches the temperature of the bath, the movable clamp is moved downwardly a predetermined distance, at a draw rate, e.g., 0.3 inch per minute, causing the heated amorphous portion of the tube to be drawn, the crystallized portion resisting such deformation. A necked-down region is formed as a result of the drawing. The degree of necking and thinning of the walls depends upon the conditions of drawing, for example, the drawing rate, drawing temperature, length of the amorphous portion being drawn, and the distance of the draw, the values of which for any particular balloon can be determined by ready trial. After the initial necking down of the tube, the tube is reversed in the bath and the second necked down portion is formed by the same procedure. Thus a preform in which the thickness of the wall of the tube in the region of the draw is provided which decreases with decreasing diameter. After this preform is completed, the tube is submerged in a second bath of glycerin, this time arranged horizontally. The crystallized portion of the tube is grasped by clamps and the temperature of the bath regulated to correspond to the desired blowing temperature, e.g., 90° C. The two clamps are drawn apart, simultaneously, gas pressure is applied to the interior of the tube causing it to expand. The amorphous region of the tube expands without constraint until the molecules of the wall material in the balloon region become stabilized in a biaxially oriented condition. The portions of the tube having the preformed tapers also expand until they are constrained to the shape of constraining elements. After formation of the balloon, the balloon is cooled, dried, and the portions extending outwardly from the smallest diameter of the neck down region are cut away. The balloon is then heat set to relieve stress. This may be achieved by reinflating the balloon to 60 psi and emersing it in a water bath at about 60°-80° C., e.g., 70° C. Alternatively, the balloon may be placed in a mold of complementary shape and size, inflated to 60 psi and heated to about 140°-160° C., e.g., 150° C. for one minute. The balloon may be assembled upon a suitable catheter.

EXAMPLE II

Balloons having a length of 5 cm and wall thickness as given in Table I, line 4 were formed as discussed above in Example I. In the tests below, the balloon is assembled on a mandrel system which enables inflation and measurement of burst pressure and inflation diameters. Referring to Table I below and FIGS. 3-5, the strength of balloons measured by the burst and hoop stress, as well as the compliance of the balloons as measured indirectly by the inflated outer diameter and inflated length are compared for balloons formed, respectively from 100% PET, 90% PET and 10% Selar PT, and 80% PET and 20% Selar PT. Burst pressure (FIG. 3, Table 1, line 6) was measured by inflation of balloons to bursting; hoop stress at failure (FIG. 4, Table 1, line 7) was calculated using hoop stress equations as well-known; compliance was measured in several forms: the outer diameter (OD at 30 psi) was measured (Table 1, line 9); the percent change of inflated outer diameter at 60 psi and 30 psi (FIG. 5, Table 1, line 10) and 90 psi and 30 psi (FIG. 5, Table 1, line 11) were measured as well as the percentage change in inflated length at 60 psi and 30 psi (FIG. 5, Table 1, line 12) and 90 psi and 30 psi (FIG. 5, Table 1, line 13). Table 1 also indicates in columns G, H, and I the significance of the differences in values tested between the various balloons.

TABLE 1

| | A | B | C | D | E | F | G | H | I |
|---|---|---|---|---|---|---|---|---|---|
| 1 | | | | | | | SIGNIFICANT | DIFFERENCE IN | TEST RESULTS? |
| 2 | | | | | | | | | |
| 3 | DESCRIPTION | N = | 100% PET | 90/10 PET:SEL | 80/20 PET:SEL | | 100 vs 90/10 | 100 vs 80/20 | 90/10 vs 80/20 |
| 4 | THICKNESS (INCHES) | | 0.00065 | 0.0006 | 0.00065 | | | | |
| 5 | NO. OF TESTS RUN: | | 11 | 7 | 10 | | | | |
| 6 | BURST PRESSURE - PSI | | 231 | 171 | 180 | | YES | YES | NO |
| 7 | HOOP STRESS (PSI) | | 40346 | 36844 | 39028 | | YES | NO | NO |
| 8 | | | | | | | | | |
| 9 | COMPLIANCE: | OD @ 30 = PSI | .226 | .253 | .255 | | | | |
| 10 | % OD 60/30 | | 2.6 | 3.9 | 4.1 | | NO | YES | NO |
| 11 | % OD 90/30 | | 4.4 | 6.2 | 6.9 | | YES | YES | NO |
| 12 | % L 60/30 | | 1.4 | 2.7 | 2.8 | | YES | YES | NO |
| 13 | % L 90/30 | | 2.5 | 4.3 | 4.9 | | YES | YES | NO |

Figure 4:
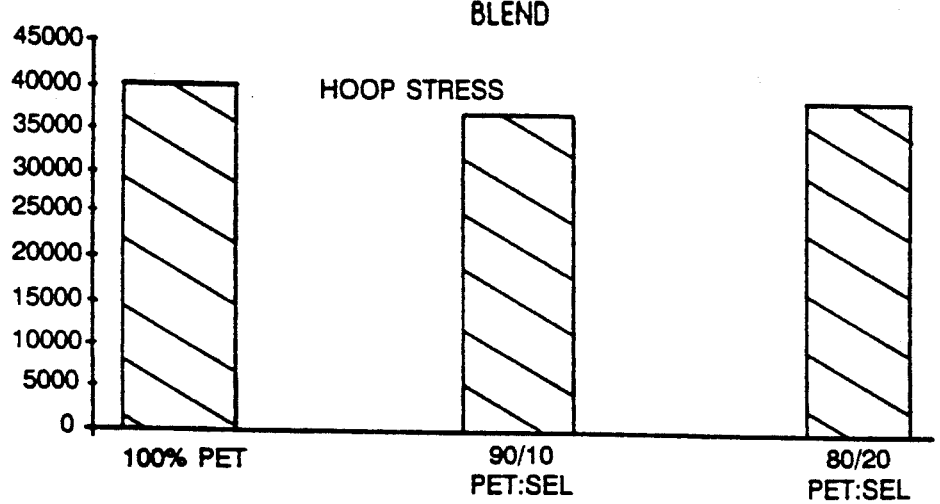
FIG. 4 is a bar graph comparing the hoop stress for the balloons as in FIG. 3.
Figure 5:
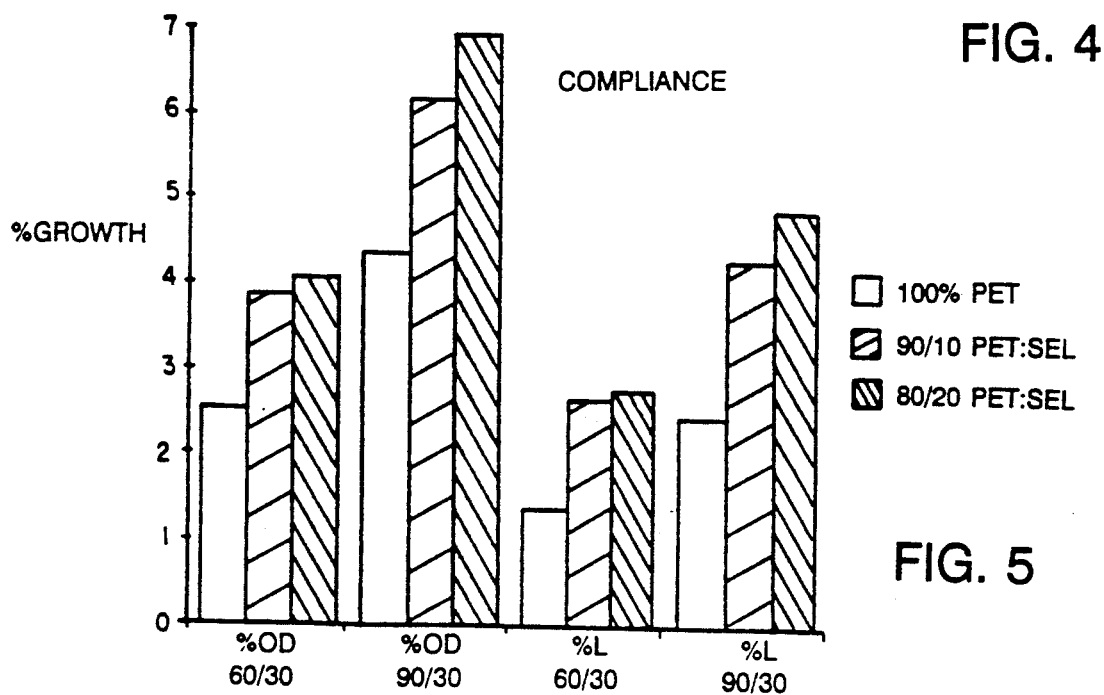
FIG. 5 is a bar graph comparing the compliance of the balloons as in FIG. 3, as measured by increased inflation length (L) and outer diameter (OD).

In FIGS. 3 and 4 and Table 1, lines 6 and 7, the strength of the balloons are compared. Referring to FIG. 3, a bar graphical representation of the burst pressures indicated in Table 1, line 6 for the balloon formed of 100% PET and blends of PET and the additive are shown. The data indicates that only a small reduction in burst pressure is observed for balloons including the additive compared to the balloon formed from 100% PET. In FIG. 4, the hoop stress at failure of the balloons is compared in bar graphical form. Similarly, the balloons incorporating a blend of additive with PET do not exhibit substantially reduced hoop stress compared to the balloon formed of 100% PET. In the case of balloons incorporating an additive, the hoop stress at failure decreased less than 10% compared to the balloon formed from 100% PET.

In FIG. 5 and Table 1, lines 9-13, the compliance of the balloons is compared by indirect measurements. Referring now to FIG. 5, the compliance of the balloons by measurement of the percent change in inflation outer diameter and length at different pressures (60 psi versus 30 psi and 90 psi versus 30 psi) as in Table 1, lines 10-13 is shown in bar graphical form. In each case, the balloons formed according to the invention, including an additive, show greater percentage inflated size than a balloon formed from 100% PET. The percentage increase for the balloons employing the additives was at least about 25% higher compared to the balloons formed from 100% PET. (For example, referring to Table 1, line 10, the change in percentage increase for the 90%/10% PET/Selar balloon compared to the 100% PET balloon is 1.3% which is a percentage increase for the additive balloon of 50% over the 100% PET balloon.) Referring to Table 1, line 9, the inflation diameter of the balloons at 30 psi are given. The balloons including an additive show greater inflation diameter than balloons formed from 100% PET.

As the results in the table and graphs indicate, for balloons employing a blend of crystalline polymer and an additive, significant improvements in compliance where observed while only small reductions in strength resulted, compared to the balloon formed from 100% PET.

OTHER EMBODIMENTS

It will be understood that balloons of varying sizes and for varying applications may be formed according to the invention, as discussed. For example, balloons of inflated diameter in the range of 2 to 8 mm, having burst pressures in the range of up to 12 atmospheres, may be formed. Other applications may employ balloons of varying sizes and strengths, as required. For example, a balloon according to the invention used for PTCA exhibiting increase in compliance and a lower folded profile is advantageous in crossing stenosis in coronary arteries.

Other embodiments are within the following claims.

We claim:

1. A medical device comprising a support member, an inflation lumen and a medical balloon mounted on said support and communicating with said lumen, the improvement comprising:
   a balloon member comprised of a polymer blend including a predominant amount of a crystalline polymer and
   a compliance enhancing additive polymer in amount sufficient to interrupt the crystalline structure of said crystalline polymer, said amount being about 20% or less of the polymer blend.

2. The device of claim 1 wherein said additive is an amorphous polymer.

3. The device of claim 2 wherein said additive is a polyolefin.

4. The device of claim 3 wherein said additive is polyethylene.

5. The device of claim 1 wherein said additive is a preblend.

6. The device of claim 5 wherein said additive is a preblend of PET and polyolefin.

7. The balloon of claim 1 or 6 wherein said additive is between about 5 to 10% of said polymer blend.

8. The device of claim 5 wherein said additive is a preblend of PET and polyethylene.

9. The device of claim 1 wherein said additive is immiscible with said crystalline polymer.

10. The device of claim 9 wherein said additive forms domains within said blend.

11. The device of claim 1 wherein said additive is a crystalline polymer.

12. The device of claim 11 wherein said additive is a liquid-crystal polyester material.

13. The balloon of claim 1 wherein said crystalline polymer is high molecular weight PET.

14. The balloon of claim 13 wherein said PET has an intrinsic viscosity of about 0.7 or greater.

15. The balloon of claim 1 wherein said balloon wall has a thickness of about 0.0015 inch or less.

16. The balloon of claim 15 wherein said balloon has a burst pressure of more than 6 atmosphere.

17. The balloon of claim 15 wherein said balloon has a burst pressure of 4 to 8 atmosphere.

18. The device of claim 1 wherein said additive is miscible with said crystalline polymer.

19. The balloon of claim 1 wherein said balloon is sized for dilatation of the prostate.

20. The balloon of claim 1 wherein said balloon has a hoop stress at failure of greater than about 36,000 psi.

21. The balloon of claim 1 wherein said balloon exhibits enhanced compliance over PET of about 25% or more with decreased hoop stress of about 10% or less.

22. The balloon of claim 1 wherein said balloon of said polymer blend is formed by free inflation under conditions to biaxially orient said crystalline polymer.

23. In a method for forming a medical device comprising a supporting member, an inflation lumen and a medical balloon mounted on said support and communicating with said lumen, the improvement comprising:
    preparing a polymer blend of a predominant amount of a crystalline polymer with a compliance enhancing additive polymer in amount sufficient to interrupt the crystalline structure of said crystalline polymer, said amount being about 20% or less of the polymer blend, and
    forming said blend into a balloon.

24. The method of claim 23 wherein said preparing comprises blending a crystallizable polymer with said additive, and
    then crystallizing said crystallizable polymer.

25. The method of claim 23 or 24 wherein said forming comprises forming said balloon of said polymer blend by free inflation under conditions to biaxially orient said crystalline polymer.

26. The method of claim 25 further comprising blending said crystalline polymer with an additive in the form of a preblend.

27. The method of claim 26 wherein said preblend is a preblend of PET and polyolefin.

28. A medical device comprising a supporting member, an inflation lumen and a medical balloon mounted on said support and communicating with said lumen, the improvement comprising:
    a balloon member comprised of a polymer blend including a predominant amount of PET, and
    a compliance enhancing additive polymer in amount sufficient to interrupt the crystalline structure of said PET, said amount being about 20% or less of the polymer blend.

29. The device of claim 28 wherein said additive is a preblend of PET and polyolefin.

30. A dilation catheter, comprising:
    a catheter shaft carrying at its distal end a dilation balloon which can be inflated,
    said balloon comprised of a polymer blend including a predominant amount of a crystalline polymer and
    a compliance enhancing additive polymer in amount sufficient to interrupt the crystalline structure of said crystalline polymer, said amount being about 20% or less of the polymer blend.

* * * * *